United States Patent [19]

Huang et al.

[11] Patent Number: 5,600,050
[45] Date of Patent: Feb. 4, 1997

[54] ZEOLITE CATALYST FOR THE LIQUID PHASE ALKYLATION AND TRANSALKYLATION OF BENZENE

[75] Inventors: Zhiyuan Huang; Suxian Tian; Yali Xu; Bin Zhu; Weidong Wang; Fengmei Zhang; Xie Wang, all of Beijing, China

[73] Assignees: ChinaPetro-Chemical Corp.; Research Institute of Petroleum Processing, both of Beijing, China

[21] Appl. No.: 355,877

[22] Filed: Dec. 14, 1994

[51] Int. Cl.$^6$ ................................ C07C 2/70
[52] U.S. Cl. ............... 585/462; 585/463; 585/470; 585/475
[58] Field of Search .................. 502/64, 85, 86; 585/446, 462, 463, 467, 470, 475

[56] References Cited

U.S. PATENT DOCUMENTS

| | | | |
|---|---|---|---|
| 4,891,458 | 6/1990 | Innes et al. | 585/323 |
| 5,430,198 | 7/1995 | Knitton et al. | 568/698 |

*Primary Examiner*—Michael Lewis
*Assistant Examiner*—Thomas G. Dunn Jr.
*Attorney, Agent, or Firm*—Pennie & Edmonds

[57] ABSTRACT

Disclosed is a modified zeolite catalyst for the liquid phase alkylation and transalkylation of benzene comprising 30 to 70% by weight of H-beta zeolite with a silicon to aluminium ratio of 20 to 40; 0.5 to 10% by weight of halogen; and $\gamma$-$Al_2O_3$ of the balance. Also disclosed a method for preparing the said catalyst comprising adding a halogen-containing compound to a mixture of H-beta zeolite and a precursor of $\gamma$-$Al_2O_3$, forming followed by calcining.

4 Claims, No Drawings

ZEOLITE CATALYST FOR THE LIQUID PHASE ALKYLATION AND TRANSALKYLATION OF BENZENE

FIELD OF THE INVENTION

The present invention relates to a zeolite catalyst for the liquid phase alkylation and transalkylation of benzene, more particularly, to a modified zeolite beta catalyst for the production of ethylbenzene or cumene from the liquid phase alkylation of benzene with ethylene or propylene and the production of monoalkylated benzene from the transalkylation of benzene with polyalkylbenzene.

BACKGROUND OF THE INVENTION

Early developed catalysts for the alkylation and/or transalkylation of benzene are of Friedel-Crafts type, such as aluminium chloride, boron trifluoride, hydrofluoric acid. However, such catalysts bring about various problems such as separation of the catalyst from the product, corrosion of the process equipment and the three-waste pollution in industrial processes.

Such catalysts have been replaced or are being replaced by solid acid catalyst, especially zeolite catalyst, such as ZSM-5 zeolite employed in vapor phase process, ultrastable Y zeolite and zeolite beta employed in liquid phase process. U.S. Pat. No. 4,891,458 describes in detail a process of alkylation of benzene with $C_2$ to $C_4$ olefin or transalkylation of benzene with polyalkylbenzene using zeolite beta as catalyst. The catalyst used in the process are as follows. The pure zeolite beta may be used as a catalyst, but generally the catalyst comprises from 1 to 99% by weight, preferably from 10 to 90% by weight, more preferably from 60 to 80% by weight of zeolite beta in admixture with an inorganic oxide binder such as alumina, silica, silica/alumina, or naturally occurring clays. The zeolite beta used has a silicon to aluminium ratio of 5 to 100, preferably 5 to 50. It can be of Na type as-synthesized, or of a type of a metal ion selected from Groups IA, II A or III A, such as ions of lithium, potassium, calcium, magnesium, lanthanum, cerium, nickel, platinum, palladium, and the like, which is incorporated by ion exchange technique. However, for high catalytic activity, the zeolite beta should be predominantly of its H type, preferably at least 80 percent of the cation sites are occupied by hydrogen ions and/or rare earth ions. The zeolite beta catalyst can provide monoalkylated products in high yield and high product purity, and provide high yields of monoalkylated product for much longer periods of time than other zeolite catalysts.

Some patents report modification of zeolite-alumina catalyst with fluoride. For example, treatment of formed catalyst of ZSM type zeolite and alumina with fluoride, such as hydrofluoric acid, sodium fluoride, potassium fluoride, lithium fluoride, boron trifluoride, ammonium fluoride, increases remarkably the cracking activity ($\alpha$value) of the catalyst (U.S. Pat. Nos. 4,427,786; 4,564,719; 4,538,014; 4,538,016; EP 134, 326 ) EP295, 020 discloses the treatment of deactivated zeolites such as zeolite USY, ZSM-5, beta with aqueous solution of $NH_4F$ . HFimproves their cracking activity ($\alpha$value) EP295, 019 discloses that zeolites such as USY, ZSM-5 and beta are treated with aqueous solution of $NH_4F$ . HF to remove non-frame work aluminium from their crystals and thus improved in their crystallinity.

However, there is no report up to now on the use of modified zeolite catalyst with halogen-containing compound in the alkylation or transalkylation of benzene.

SUMMARY OF THE INVENTION

An object of the invention is, based on the catalysts of the prior art, to provide a modified zeolite catalyst which shows higher space-time yield and selectivity of monoalkylated benzene in the production of ethylbenzene or cumene from the liquid phase alkylation of benzene with ethylene or propylene and the production of monoalkylated benzene from the transalkylation of benzene with polyalkylbenzene, and higher conversion of polyalkylbenzene in the latter.

Another object of the invention is to provide a method for preparing the modified zeolite catalyst.

The invention provides a catalyst of the following composition: 30 to 70% by weight of H-beta zeolite with a silicon to aluminium ratio of 20 to 40; 0.5 to 10% by weight of halogen; and $\gamma$-$Al_2O_3$ of the balance, based in each case on the total weight of the catalyst.

The catalyst is prepared by adding a halogen-containing compound to a mixture of H-beta zeolite and a precursor of $\gamma$-$Al_2O_3$, forming followed by calcining.

The catalyst of the invention can provide higher space-time yield and selectivity of monoalkylated benzene in the production of ethylbenzene or cumene from the liquid phase alkylation of benzene with ethylene or propylene and the production of monoalkylated benzene from the transalkylation of benzene with polyalkylbenzene, and higher conversion of polyalkylbenzene in the latter.

DETAILED DESCRIPTION OF THE INVENTION

The invention provides a catalyst of the following composition: 30 to 70% by weight of H-beta zeolite with a silicon to aluminium ratio of 20 to 40; 0.5 to 10%, preferably 1 to 5% by weight of halogen; and $\gamma$-$Al_2O_3$ of the balance, based in each case on the total weight of the catalyst.

The "zeolite beta" said herein refers mainly to the zeolite defined by the X-ray diffraction pattern in U.S. Pat. No. 3,308,069, or refers to those described in European Patent Application Nos. 55, 046 ("Nu-2")and 64, 328 and British Patent Application No. 2, 024, 790 ("Boralite B") which have X-ray diffraction patterns very similiar to that described in the U.S. Patent. But the method of synthesis is not limited by the above patents.

The "halogen" said herein is selected from fluorine, chlorine, bromine, preferably fluorine.

The catalyst of the invention is prepared by adding a halogen-containing compound to a mixture of H-beta zeolite and a precursor of $\gamma$-$Al_2O_3$, forming followed by calcining. The steps are as follows:

1. The synthetic Na-beta zeolite is converted to its H form by ammonium exchange followed by calcination;
2. To a mixture of H-beta zeolite and a precursor of $\gamma$-$Al_2O_3$ a halogen-containing compound is added and the mixture is formed;
3. The formed product is calcined at a temperature of 450° to 600° C.

The precursor of $\gamma Al_2O_3$ used in the process refers to boehmite or pseudo-boehmite. Halogen-containing compound may be fluorine-, chlorine-, or bromine-containing compound, preferably fluorine-containing compound, such as boron trifluoride, ammonium fluoroborate, hydrofluoric acid, ammonium fluoride, ammonium fluorosilicate, trifluoroacetic acid, trifluoroethanol, and the like.

The catalyst of the invention is useful in the liquid phase alkylation and transalkylation of benzene. Especially when the catalyst is used in the production of ethylbenzene or cumene from the alkylation of benzene with ethylene or propylene or the transalkylation of benzene with polyethylbenzene or diisopropylbenzene, it shows higher space-time yield and selectivity of ethylbenzene or cumene as well as higher conversion of polyethylbenzene or diisopropylbenzene than that of H-and/or RE-beta-alumina catalyst of the prior art. For example, the catalyst of the invention increases the space-time yield of ethylbenzene by 17 to 20%, and the selectivity of ethylbenzene by 1.2 to 2.4% when the alkylation is carried out under a condition of a temperature of 200° C., a pressure of 2.94 MPa, and a benzene/ethylene molar ratio of 8:1; it increases the space-time yield of ethylbenzene by 15.0% , the conversion of diethylbenzene by 5.0%, and the conversion of polyethylbenzene by 5.1% when the transalkylation is carried out under a condition of a temperature of 250° C., a pressure of 3.92 MPa, and a bezene/polyethylbenzene molar ratio of 10:1; and it increases the space-time yield of cumene by 15.4%, and the selectivity of cumene by 3.2% when the alkylation is carried out under a condition of a temperature of 160° C., a pressure of 3.5 MPa, a liquid hourly space velocity of benzene of 6.0, and a benzene/propylene molar ratio of 6:1.

The invention is further illustrated by the following examples but not limited by them in any way.

EXAMPLES 1 to 3

Preparation of the catalyst of the present invention Na-beta zeolite with a silicon to aluminium ratio of 20 to 40 and sodium oxide content of 0.8% by weight was ammonium exchanged with 1N aqueous solution of ammonium sulfate at 90° C. for two hours. Free sulfate ion-was washed out, and the resulted material was dried at 110°±10° C., calcined at 550° C. for six hours to give H-beta zeolite.

The obtained H-beta zeolite was mixed with SB-aluminium hydroxide (Condea, Germany) in a weight ratio of zeolite: alumina=1:1. Ammonium fluoride was added to three portions of such mixtures in an amount that the fluorine content in the catalyst samples obtained was 1, 3 and 5% by weight respectively. After addition of the decationized water (q.v.) the resulted mixtures were kneaded and extruded to extrudates of 1.5 mm in diameter, which were dried at 110°±10° C. for twelve hours, then calcined in a muffle furnace at 550° C. for six hours.

COMPARATIVE EXAMPLE 1

H-beta-alumina catalyst sample was prepared by the same method described in examples 1 to 3 except that no ammonium fluoride was added.

COMPARATIVE EXAMPLE 2

Na-beta zeolite (the same type as in examples 1 to 3) was ion exchanged with 1N aqueous solution of lanthunum nitrate at 95° C. for two hours. Free nitrate ion was washed out, and the resulted material was dried at 110°±10° C., calcined at 550° C. for six hours to give La-beta zeolite.

La-beta-alumina catalyst sample was prepared by the same method described in examples 1 to 3 except that no ammonium fluoride was added.

EXAMPLE 4

This example illustrates the use of the catalyst of the invention in the alkylation of benzene with ethylene.

The above five catalyst samples were evaluated in a CDS-900 fixed bed microreactor system (Chemical Data systems, U.S.A.) by using benzene and ethylene as starting materials. 8 ml of catalyst sample of 16 to 20 mesh was diluted with 22 ml of inert quartz sand of the same size, then was charged into the reactor. The reaction was carried out under a condition of a temperature of 200° C., a pressure of 2.94 MPa, and a benzene/ethylene molar ratio of 8. The result is shown in table 1.

TABLE 1

| Catalyst | Example 1 | Example 2 | Example 3 | Comparative Example 1 | Comparative Example 2 |
|---|---|---|---|---|---|
| $C_F$, wt % | 1 | 3 | 5 | 0 | 0 |
| STY, gEB/kg cat. · h | 970 | 990 | 992 | 825 | 854 |
| $\Delta$STY, % | +17.6 | +20.0 | +20.2 | base | +3.5 |
| $S_{EB}$, % | 92.4 | 93.5 | 92.5 | 91.3 | 84.7 |
| $\Delta S_{EB}$, % | +1.2 | +2.4 | +1.3 | base | −7.2 |
| $S_E$, % | 99.3 | 99.4 | 99.3 | 98.9 | 94.5 |

In this table, $C_F$ is the fluorine content of the catalysts; STY is the space-time yield of ethylbenzene; $\Delta$STY is the relative increment of the space-time yield of ethylbenzene; $S_{BB}$ is the selectivity of ethylbenzene; $\Delta S_{EB}$ is the relative increment of the selectivity of ethylbenzene; $S_B$ is the selectivity of the ethylation of benzene.

As shown from table 1, the catalysts of the invention provide an increase in the space-time yield of ethylbenzene from 17 to 20%, and an increase in the selectivity of ethylbenzene from 1.2 to 2.4% in the ethylation compared to the catalysts of the prior art.

EXAMPLE 5

This example illustrates the use of the catalyst of the invention in the transalkylation of benzene with polyethyl benzene.

The catalyst samples of example 1 and comparative example 1 were evaluated in the same apparatus described in example 4 by using benzene and polyethylbenzene (containing about 90% by weight of diethylbenzene, and triethylbenzene and polyethylbenzene of the balance) as starting materials. The particle size, amount and charging manner of the catalyst sample were the same as those in example 4. The reaction temperature was 250° C., the pressure was 3.92 Ma, and the molar ratio of benzene to ethylene was 10. The result is shown in table 2.

TABLE 2

| Catalyst | Example 1 | Comparative Example 1 |
|---|---|---|
| STY, gEB/kg cat. · h | 614 | 534 |
| $\Delta$STY, % | +15.0 | base |
| $S_{EB}$, % | >99 | ≧98 |
| $X_{DEB}$, % | 81.5 | 77.6 |
| $\Delta X_{DEB}$, % | +5.0 | base |
| $X_{PEB}$, % | 78.9 | 75.1 |
| $\Delta X_{PEB}$, % | +5.1 | base |

In this table, STY and $\Delta$SYT are the space-time yield of ethylbenzene and the relative increment of STY respectively; $S_{BB}$ is the selectivsty of ethylbenzene; $X_{DEB}$ and $\Delta X_{DEB}$ are the conversion of diethylbenzene and the relative increment of $X_{DEB}$ respectively ; $X_{PEB}$ and $\Delta X_{PEB}$ are the conversion of polyethylbenzene and the relative increment of $X_{PEB}$ respectively.

As shown from table 2, the catalyst of the invention provides an increase in the space-time yield of ethylbenzene of 15.0%, an increase in the conversion of diethyl-benzene of 5.0%, and an increase in the conversion of polyethylbenzene of 5.1% in the transethylation compared to the catalyst of the prior art.

EXAMPLE 6

This example illustrates the use of the catalyst of the invention in the alkylation of benzene with propylene.

The catalyst samples of example 1 and comparative example 1 were evaluated in the same apparatus described in example 4 by using benzene and propylene as starting materials. The particle size, amount and charging manner of the catalyst sample were the same as-those in example 4. The reaction temperature was 160° C., the pressure was 3.5 MPa, the liquid hourly space velocity of benzene was 6.0, and the molar ratio of benzene to propylene was 6. The result is shown in table 3.

TABLE 3

| Catalyst | Example 1 | Comparative Example 1 |
|---|---|---|
| STY, g cumene/kg cat. · h | 1551 | 1344 |
| ΔSTY, % | +15.4 | base |
| Sc, % | 94.4 | 91.5 |
| ΔSc, % | +3.2 | base |
| Sp, % | 99.4 | 99.3 |

In this table, STY and ΔSTY are the space-time yield of cumene and the relative increment of STY respectively; Sc and ΔSc are the selectivity of cumene and the relative increment of Sc respectively: Sp is the selectivity of the propylation of benzene.

As shown from table 3, the catalyst of the invention provides an increase in the space-time yield of cumene of 15.4%, and an increase in the selectivity of cumene of 3.2% in the propylation compared to the catalyst of the prior art.

We claim:

1. The process of producing ethylbenzene comprising alkylating benzene with ethylene in the presence of a catalyst under conditions effective for the production of ethylebenzene and recovering the product, wherein the catalyst is a zeolite catalyst for the liquid phase alkylation and transalkylation of benzene comprising 30 to 70% by weight of H-beta zeolite with a silicon to aluminum ration of 20 to 40; 0.5 to 10% by weight of halogen; and the balance gamma alumina, based in each case on the total weight of the catalyst, and the catalyst is prepared by the process comprising contacting a halogen-containing compound with a mixture of H-beta zeolite and a precursor of gamma alumina.

2. The process of process of producing ethylbenzene comprising transalkylating benzene with polyethylbenzene in the presence of a catalyst under conditions effective of the production of ethylbenzene and recovering the product, wherein the catalyst is a zeolite catalyst for the liquid phase alkylation and transalkylation of benzene comprising 30 to 70% by weight of H-beta zeolite with silicon to aluminum ration of 20 to 40; 0.5 to 10% by weight of halogen; and the balance gamma alumina, based on each case on the total weight of the catalyst, and the catalyst is prepared by the process comprising contacting a haolgen-containing compound with a mixture of H-beta zeolite and a precursor of gamma alumina.

3. The process of producing cumene comprising alkylating benzene with propylene in the presence of a catalyst under conditions effective for the production of cumene and recovering the product, wherein the catalyst is a zeolite catalyst for the liquid phase alkylation and transalkylation of benzene comprising 30 to 70% by weight of H-beta zeolite with a silicon to aluminum ration 20 to 40; 0.5 to 10% by weight of halogen; and the balance gamma alumina, based in each case on the total weight of the catalyst, and the catalyst is prepared by the process comprising contacting a halogen-containing compound with a mixture of H-beta zeolite and a precursor of gamma alumina.

4. The process of producing cumene comprising transalkylating benzene with diisopropylbenzene in the presence of a catalyst under conditions effective for the production of cumene and recovering the product, wherein the catalyst is a zeolite catalyst for the liquid phase alkylation and transalkylation of benzene comprising 30 to 70% by weight of H-beta zeolite with a silicon to aluminum ratio of 20 to 40; 0.5 to 10% by weight of halogen; and the balance gamma alumina, based in each case on the total weight of the catalyst, and the catalyst is prepared by the process comprising contacting a halogen-containing compound with a mixture of H-beta zeolite and a precursor of gamma alumina.

* * * * *